United States Patent

Mejías

Patent Number: 6,070,751
Date of Patent: Jun. 6, 2000

[54] HERMETICALLY SEALED CONTAINER FOR CLINICAL RESIDUES

[75] Inventor: David González Mejías, Majadahonda, Spain

[73] Assignee: Sanypick, S.A., Madrid, Spain

[21] Appl. No.: 09/066,415

[22] PCT Filed: Aug. 30, 1996

[86] PCT No.: PCT/ES96/00165

§ 371 Date: Sep. 2, 1999

§ 102(e) Date: Sep. 2, 1999

[87] PCT Pub. No.: WO98/08560

PCT Pub. Date: Mar. 5, 1998

[51] Int. Cl.[7] ............................. A61M 5/32; A61B 19/02; B65F 1/16
[52] U.S. Cl. .......................... 220/253; 220/254; 220/820; 220/910; 206/365
[58] Field of Search .................................. 220/253, 254, 220/255, 315, 324, 326, 789, 790, 820, 824, 345.1, 345.2, 345.4, 910; 206/365, 366, 1.5

[56] References Cited

U.S. PATENT DOCUMENTS

| | | | |
|---|---|---|---|
| 4,375,849 | 3/1983 | Hanifl | 206/366 |
| 4,657,139 | 4/1987 | Hanifl | 206/366 X |
| 4,842,138 | 6/1989 | Sandel et al. | 206/366 X |
| 4,995,871 | 2/1991 | Sasaki et al. | 206/366 X |
| 5,507,408 | 4/1996 | Mosior et al. | 206/366 X |
| 5,590,774 | 1/1997 | Roberts | 206/366 |
| 5,738,236 | 4/1998 | Brun, Jr. | 220/253 |

FOREIGN PATENT DOCUMENTS 2251423 7/1992 United Kingdom ................... 206/366

Primary Examiner—Nathan Newhouse
Attorney, Agent, or Firm—Helfgott & Karas, P.C.

[57] ABSTRACT

A container comprising a main portion (1) with variable capacity and a cover (2) which may be coupled in dovetail manner, with a leak-tight sealing and with no possibility of disassembly, the cover embodying a filling window (16) which may be shut by a rotatory disk (9) which in turn is provided with two diametrically opposite windows (17) and (19), the first of which faces the window (16) during the container-filling phases and is located diametrically opposite during the temporary-sealing phases, implementing a hermetic sealing; while in the second window there is located a blocking button (22) which, after the final filling of the container, is capable of being moved inside, immovably blocking the shutter disk (9) at the cover (8) and implementing the final, non-workable sealing of the window (16) of said cover.

5 Claims, 6 Drawing Sheets

A-B

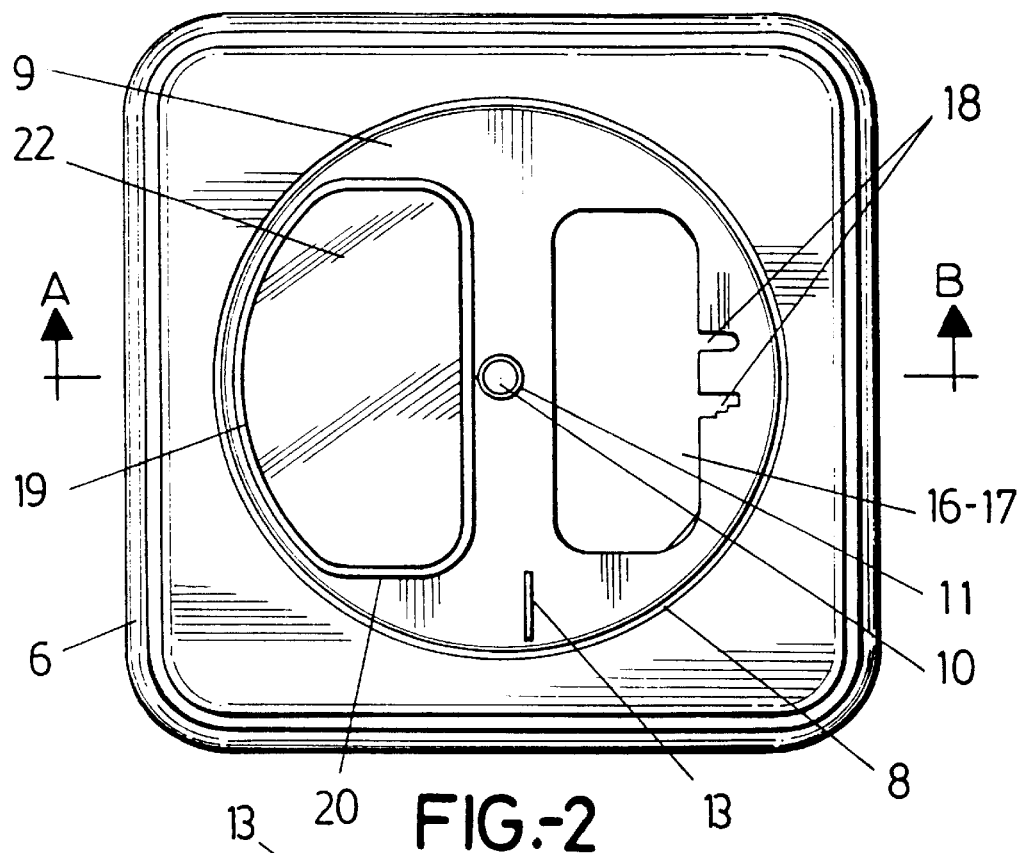
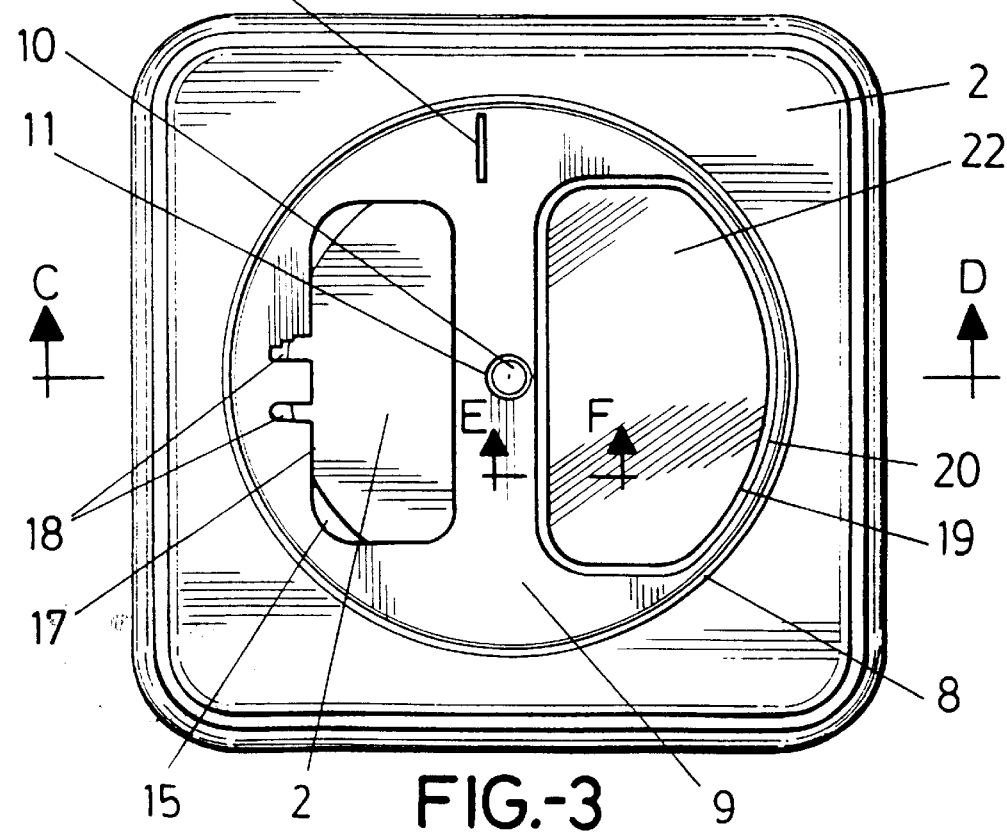

A-B

C-D

E-F

E-F

HERMETICALLY SEALED CONTAINER FOR CLINICAL RESIDUES

PURPOSE OF THE INVENTION

This invention relates to a container, which has been especially designed to hold clinical waste, equipped to form a hermetic seal, which on the one hand proves to be workable during the container-filling phase, while at the conclusion of same, said seal proves to be inviolable, ensuring an absolute inaccessibility to the clinical waste housed therein.

BACKGROUND OF THE INVENTION

In the clinical and hospital setting, waste is generated which may prove to be hazardous, sometimes because it is harmful to the health, as occurs with certain chemicals, and in other cases because it is capable of causing accidents, as happens with injection syringes and other objects.

For its disposal, this type of waste requires a container which ensures inaccessibility to the interior thereof from the clinical center in which it is produced until its final disposal.

There are known in this sense rigid or semi-rigid plastic containers, constructed with a main portion and a cover capable of being coupled hermetically, said cover furthermore being provided with a workable mouth through which the waste is poured into the interior of the container, until the latter is full, which mouth is provided with a movable shutter which makes it possible to keep the container sealed between successive manipulations for depositing of waste, which shutter, after the final filling of the container, is capable of being secured immovably, as for example through a fastening mechanism, which now makes the contents of the container inaccessible once and for all.

The containers of this type known to date do not afford optimum guarantees of leak-tightness or of inviolability of the seal, or else they have very complex structures, which make them very considerably more expensive.

DESCRIPTION OF THE INVENTION

The hermetic container for clinical waste which the invention proposes constitutes a simple and effective solution, which ensures on the one hand an optimum leak-tightness in the coupling between cover and main portion, and which similarly also affords optimum conditions of leak-tightness during the period of use of the container; that is, during the period of receiving of clinical waste until its filling, with the possibility of easy access to its interior, moreover having means for final sealing which make it absolutely inviolable.

Accordingly and more concretely, the container which is contemplated is constructed based on a main portion provided in the area of its mouth with a skirt arched outward and downward, which main portion is completed with a cover which, also at its mouth, embodies a narrow groove in which the mouth of the main portion fits tightly, from the outer edge of which groove there projects another arched skirt, complementary of that of the main portion; that is, positioned in the same direction, but of greater length and with an inner perimetria flange designed to extend beyond the free edge of the skirt of the main body, so that cover and main body prove to be easy to couple by mere pressure, but their subsequent separation proves to be extremely difficult, practically impossible.

On the other hand, the cover is provided with a circumferential groove, with a throttled mouth, in the cavity of which there moves a disk mounted freely rotatable on the cover in contact with the center of the aforementioned circumferential groove, which disk has a perimetria flange which fits through pressure into the aforementioned groove, so that said disk can rotate freely with respect to the cover itself, but remains immobilized in the axial direction.

In order to achieve this rotatory movement of the disk with respect to the cover, said disk has a manually activated outer fin, located on its periphery, and with an inner lug which moves in a second groove of the cover, in this case semi-circumferential, the ends of which act as rotation-limiting stops for the disk which, consequently, is capable of rotating only approximately 180°, in one or the other direction.

This relative rotatory movement between disk and cover has as its purpose that two ample windows, implemented on the cover and on the disk, are capable of being positioned facing one another in order to make possible the depositing of waste inside the container, or moved out of phase 180° in order to implement the sealing, temporary as well as permanent, of the container.

With respect to the aforementioned windows, it should be pointed out that the window corresponding to the rotatory disk, which is the outer window, embodies a pair of notches on one of its edges, which facilitate the freeing of hypodermic needles from the corresponding injection syringe, and other similar manipulations.

In order to implement the final, inviolable sealing of the container, it has been provided that the aforementioned disk embody a second window, positioned out of phase 180° with respect to the first, coinciding in shape with that of the cover itself and slightly oversized with respect to the latter, this second window extending outward in a short throttled-mouth neck, in which there moves a blocking button, coinciding in shape and size with said neck, forming a kind of cup the mouth of which is capable of being tightly coupled in a narrow perimetric groove with which the orifice in the cover is provided, while in the cavity of said cup are provided numerous hooks, inactive in the normal rotation of the disk with respect to the cover but which, when downward pressure is exerted on this blocking button, extend beyond the mouth of the orifice of the cover, bringing about the immovable securing of the button thereon, and consequently the immovable securing of the shutter disk, which no longer can withdraw from the sealing position, inasmuch as the retraction of the blocking button from the outside proves to be impossible.

There is achieved in this manner a container the cover of which can be coupled to main portions of different capacities, an immovable fastening being implemented between these elements, on which cover there in turn is implemented a shutter which makes it possible to open the container as many times as may be necessary during its filling, under conditions of leak-tight sealing, and which at the conclusion of the container-filling stage makes possible a final blocking of same, rendering the inside of the container completely inaccessible.

DESCRIPTION OF THE DRAWINGS

To complete the description which is being given and for the purpose of aiding in a better understanding of the characteristics of the invention, there is attached to this descriptive statement, as an integral part thereof, a set of drawings in which, with an illustrative and non-limitative nature, the following has been represented:

FIG. 2. Shows a view from above of the container in the preceding figure, in open position.

FIG. 3. Shows a view similar to that of FIG. 2, but with container in a sealed position.

PREFERRED EMBODIMENT OF THE INVENTION

Figure 1:
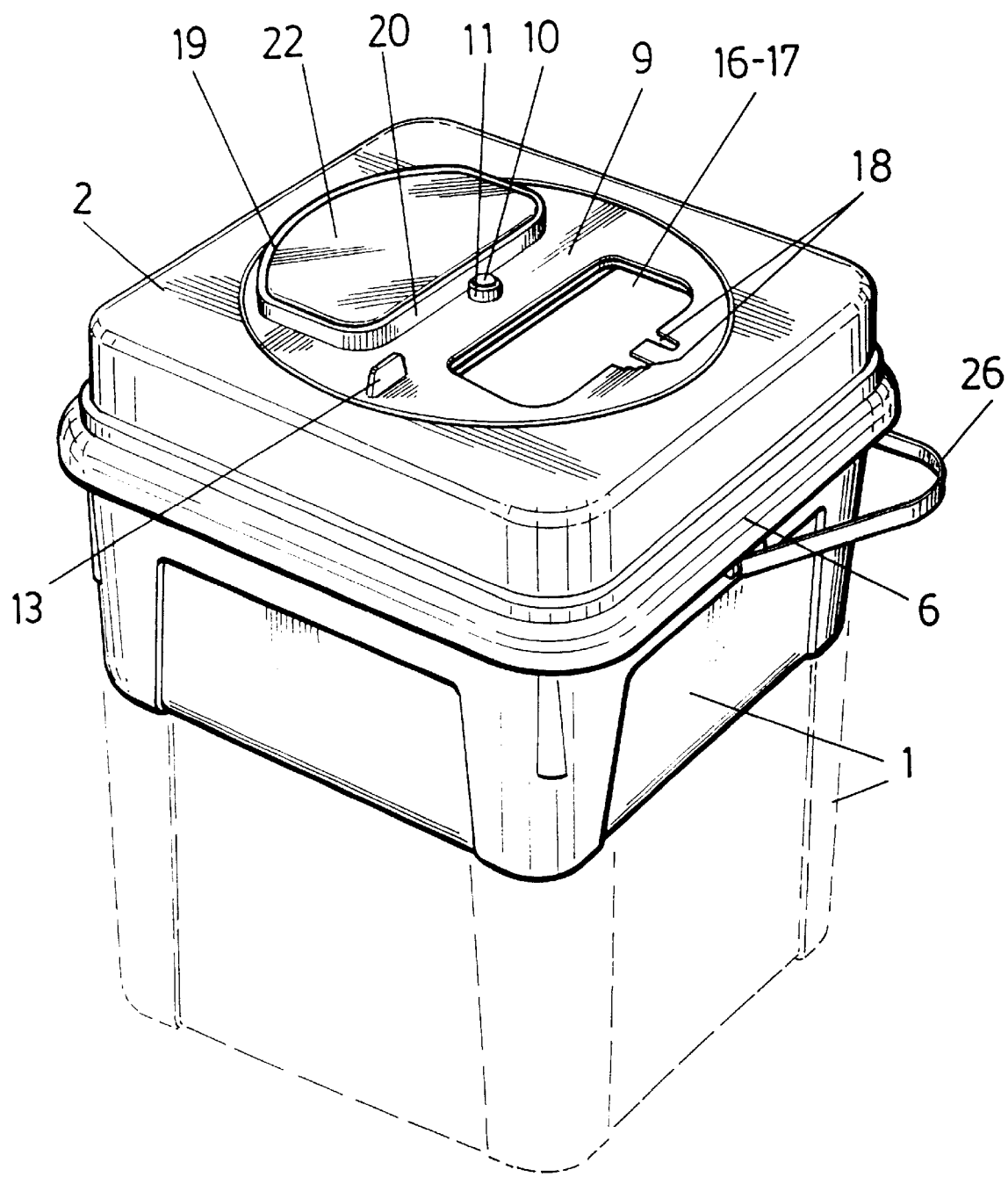
FIG. 1. Shows, in a perspective view, a hermetic container for holding clinical waste implemented in accordance with the purpose of this invention, another with larger capacity having been represented in a broken line.

On viewing these figures it may be seen how the container which is considered is formed on the basis of a main portion (1), with variable capacity, which in this case assumes a prismatic-quadrangular shape with rounded edges, but which also could assume a prismatic-rectangular shape or cylindrical shape, which main portion is completed with a cover (2) which can be coupled to same in a hermetic and immovable manner, for which purpose the main portion (1) has an outer, arching skirt (3), close to its mouth (4), while the cover has a narrow groove (5), of considerable depth, accommodating the mouth (4) of the main portion, and the outer wall of which extends in a skirt (6), also arched outward and downward like the skirt (3) of the main portion, but larger in size than the latter and provided with an inner perimetric flange (7) designed to adjust to the free edge of the skirt (3) of the main portion, as is seen in particular in FIG. 3, there being achieved in this manner a dovetailing between cover and main portion which is accessed easily, by mere pressure, but the subsequent separation of which proves to be extremely difficult.

On the other hand, the cover (2) is provided on its upper base with a circumferential groove (8), with sizeable diameter and throttled mouth, preferably with a straight trapezoidal profile, so that through said groove (8) there is coupled to the cover (2) a shutter disk (9) equipped to rotate freely with respect thereto by means of a central axis implemented on a pivot (10) projecting from the cover to which there is coupled with axial retention a bushing (11) defined on the disk (9). Said disk (9) in turn has a perimetric flange (12) which moves inside the groove (8) of the cover, in such manner that the shutter disk is equipped to rotate freely with respect to the cover but remains completely immobilized in the axial direction.

Figure 4:
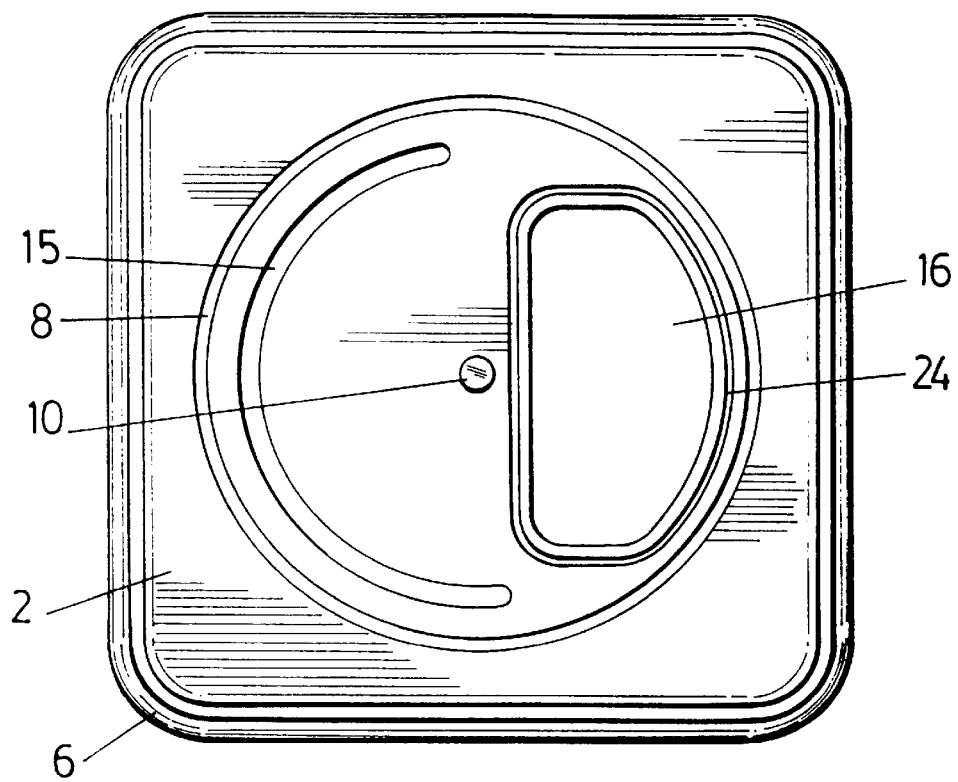
FIG. 4. Shows a view from above of the cover of the container, without the shutter disk.
Figure 5:
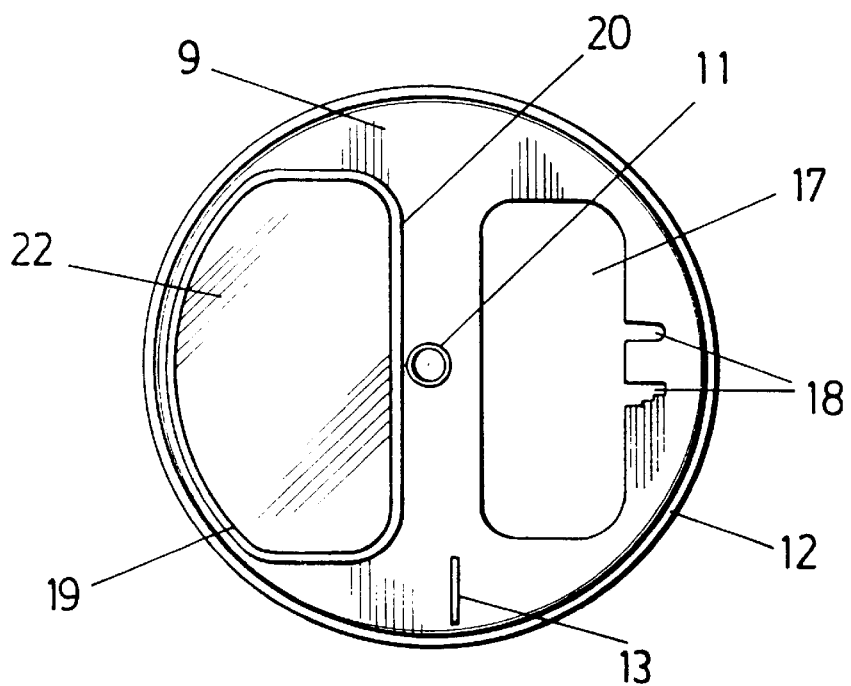
FIG. 5. Shows a view of the shutter disk from above.
Figure 6:
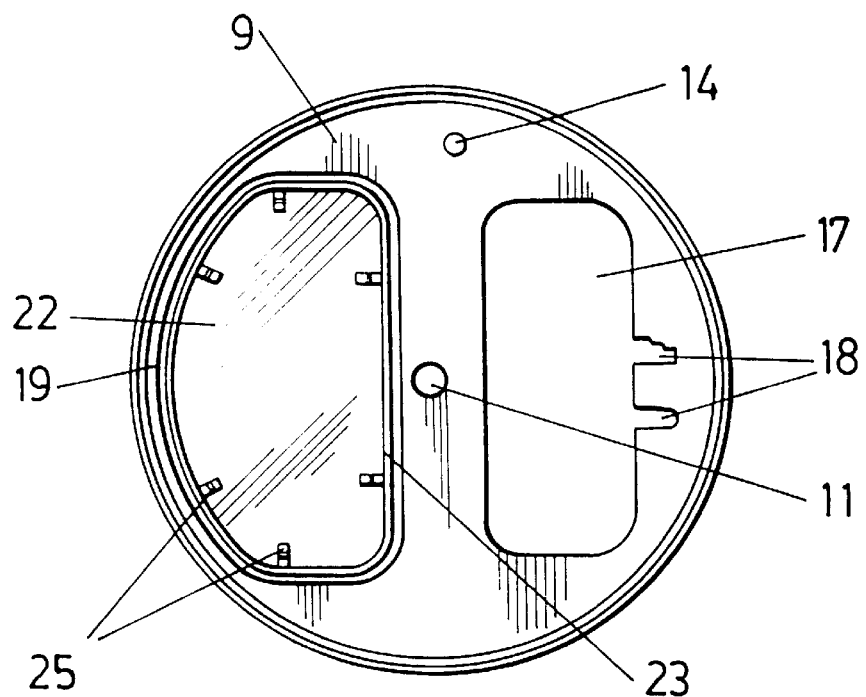
FIG. 6. Shows a view from below of the aforementioned shutter disk.
Figure 7:
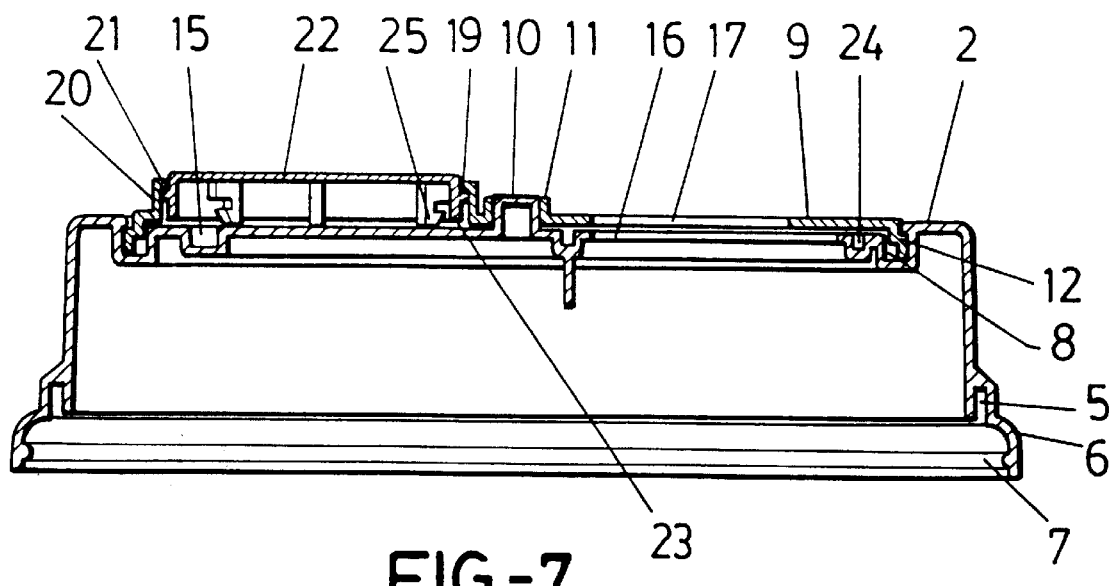
FIG. 7. Shows a detail of the cover in cross section, following the sectional line A-B of FIG. 2.
Figure 7A:
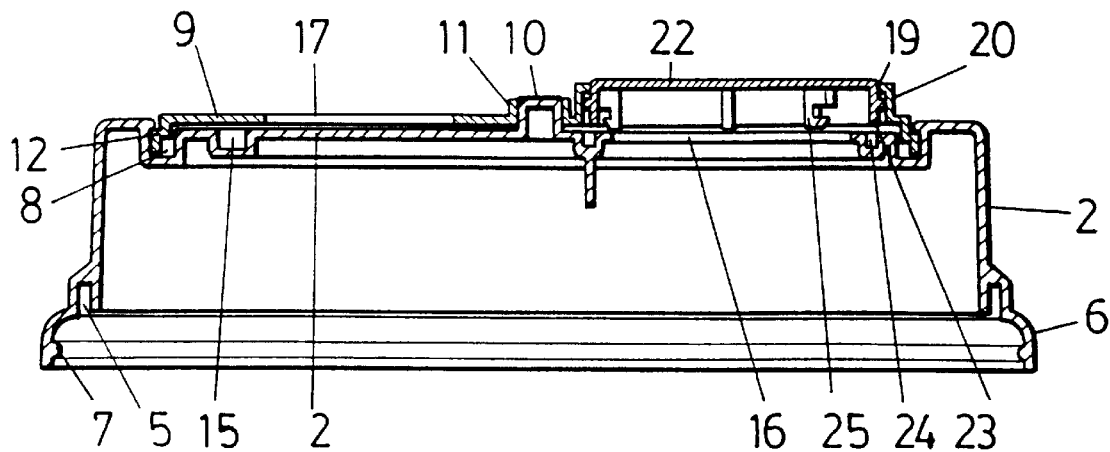
FIG. 7a. Shows the same section of the preceding figure, following sectional line C-D of FIG. 3.

Nonetheless, the rotatory movement of the shutter disk (9) is limited to 180°, for which purpose said disk has, in addition to an outer fin (13) for manual activation of same, a lower [sic: referred to elsewhere herein as inner (interior rather than inferior) ] lug (14) which moves in a groove (15) of the cover, with a semi-circumferential trajectory, as is seen in particular in FIG. 4, so that the ends of the groove (15) determine the limiting stops for rotation for the disk (9).

This limitation of rotation is positioned to achieve the result that an ample window (16) implemented on the cover (2), within the circumferential groove (8), and an ample window (17) in turn implemented on the shutter disk (9), are capable of being placed facing one another, at one of the limit positions defined by the groove (15) and the lug (14), or moved out of phase in diametrical opposition, the first position corresponding to the container opening and the second to the sealing, hermetic but workable.

In more specific manner, the window (16) of the cover (2) is basically rectangular but with its outer side markedly curvo-convex, while the window (17) of the shutter disk (9) also is rectangular but with a straight outer side, there being arranged thereon a pair of notches (18) provided to facilitate the separation of needles from their corresponding syringes, and for other similar manipulations, as stated above.

And so, in accordance with that set forth above, acting on the fin (13), the shutter (9) is capable of assuming two extreme positions, one of oppositional placement between the windows (16) and (17) or of access to the inside of the container, for depositing of waste; and the other of leak-tight temporary sealing, which prevents the escape of odors outside the container.

Figure 8:
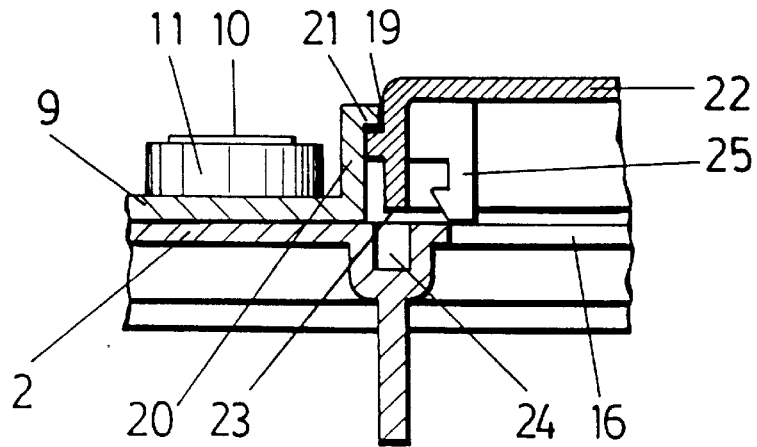
FIG. 8. Shows an enlarged detail in cross section of the coupling between cover and shutter disk, following the sectional line E-F of FIG. 3.
Figure 8A:
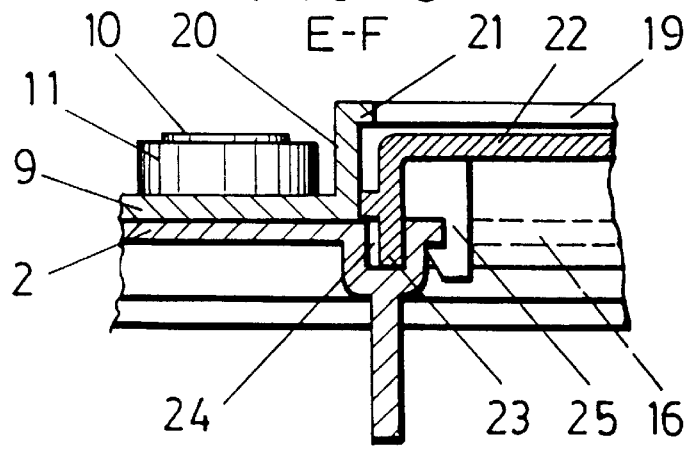
FIG. 8a. Shows the same detail of the preceding figure in position of final blocking for sealing.
Figures 9, 10:
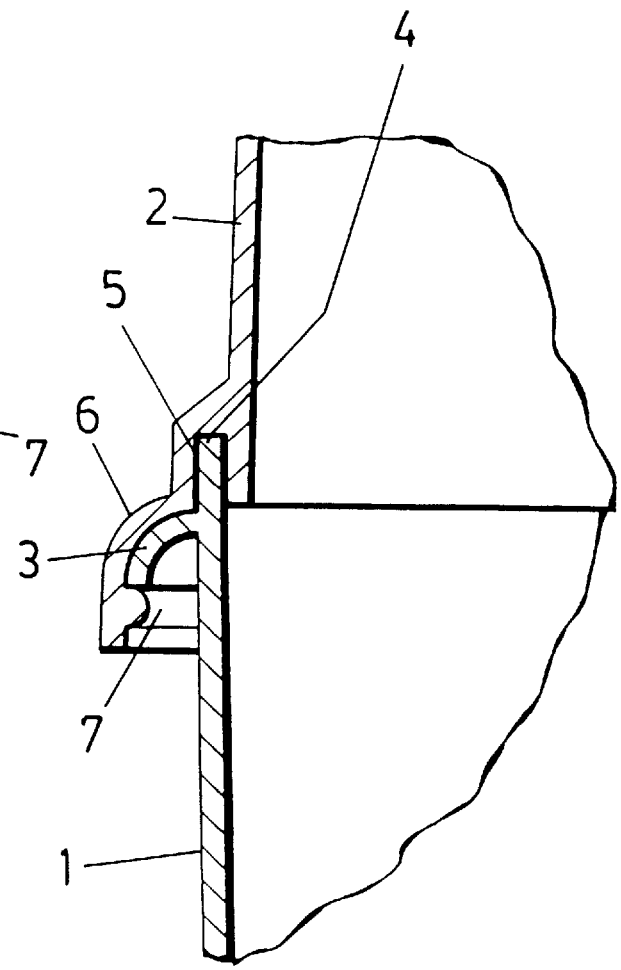
FIG. 9. Shows an enlarged detail in cross section of the area of connection between main portion and cover, in which main portion and cover appear uncoupled.
FIG. 10. Finally, shows the same detail of the preceding figure in cross section, but with the main portion and cover duly coupled.

In order to establish a final and inviolable sealing at the conclusion of the container-filling stage, it has been provided that the shutter disk (9) is equipped, opposite the window (17) for access to the inside of the container, with a second window (19), diametrically opposite with respect to the first, coinciding in shape with the window (16) of the cover (2), slightly oversized with respect to the latter, and which is positioned facing same in the container's sealing position. This window (19) extends toward the outside of a neck (20) provided with a flange (21) producing a slight throttling of same, inside of which neck (20) there moves a blocking button (22) which forms a kind of cup with concavity positioned inward, coinciding in shape and size with the neck (20), the mouth or free edge (23) of which is designed to fit tightly, when downward pressure is exerted on said button, in a groove (24) arranged functionally on the cover (2) around the window (16), the cup comprising the blocking button (22) also having a series of inner hooks (25) which, when the mouth (23) of the cup is secured in the groove (24) of the cover (2), extend beyond the mouth of the orifice (16) causing the blocking of the shutter disk, as is seen in particular in FIG. 8a, with which the sealing of the container becomes final.

And so, the blocking button (22) acts as a piston which is kept inoperative throughout the container-filling stage, making possible the free rotation of the shutter disk (9) between the limit positions of opening shown in FIG. 2 and sealing shown in FIG. 3, but which at the conclusion of the container-filling stage may be moved downward to an irreversible blocking position, which causes the sealing of the container to become final.

Finally, it remains to be noted only that, as also is seen in FIG. 1, the container is capable of bearing a handle (26) which facilitates its manipulation.

It is not considered necessary to make this description more extensive for any expert on the subject to understand the scope of the invention and the advantages which are derived therefrom.

The materials, form, size and arrangement of the elements shall be subject to variation provided it does not involve a change in the essential nature of the invention.

The wording in which this statement has been drawn up always is to be taken in a broad and non-limitative sense.

I claim:

1. Hermetic container for holding clinical waste, which being of the type of those constructed by means of a functional combination of a main portion (1) and a cover, which may be coupled in an immovable manner, and in which said cover is provided at its base with a container-filling window, aided by a rotatory shutter disk, for sealing thereof, capable of being blocked from any rotational movement in a blocking position after filling of the container, wherein the cover (2) has a circumferential groove (8), with a throttled mouth, in which there moves with axial immobilization an extended flange (12) of the shutter disk (9), said shutter disk (9) has two ample windows (17) and (19), in diametric opposition, capable of being placed, in extreme rotatory positions of the disk (9), facing the container-filling window (16) of the cover (2), one of the windows (17) of the disk (9) acting as a means of access to the container for the clinical waste, when it is placed facing the window (16) of the cover in one extreme position of the disk; while at the other extreme position of the disk the other window (19) has a blocking button (22) capable of being moved toward the inside of the container and being secured to the edge of the window (16) of the cover to prevent rotational movement of the shutter disk and block access to the container.

2. Hermetic container for holding clinical waste, in accordance with claim 1, wherein the window (19) of the shutter disk (9) bearing the blocking button (22) coincides in shape with the window (16) of the cover (2), is slightly oversized with respect to the window of the cover and has a neck (20) terminating in a small throttle (21) acting as a means of external retention of the blocking button (22), the cover (2) having a groove (24) surrounding and close to the edge of the window (16), the surrounding groove (24) coincides in shape and size to accommodate a free edge of the blocking button (22) when the blocking button is pressed in a downward direction into the blocking position, inside the free edge of the blocking button (22) there is a plurality of hooks (25) which lock with the edge of the window (16) of the cover (2) in the blocking position.

3. Hermetic container for holding clinical waste, in accordance with claim 1, wherein the shutter disk (9) has, in addition to an outer fin (13) for manual activation of same, an inner lug (14) which moves in a semi-circumferential groove (15) of the cover (2), diametrically opposite the window (16) of said cover, the ends of said groove define the limit stops for rotation for the shutter disk (9) by the lug (14).

4. Hermetic container for holding clinical waste, in accordance with claim 1, wherein the window (16) of the cover has a substantially rectangular shape, with a curvo-convex outer side, while the window (17) of the shutter disk providing means of access to the container is rectangular having an outer side that is straight, a plurality of notches (18) are located on an edge of the window (17), providing means of access to the container said plurality of notches facilitate the separation of hypodermic needles from their corresponding injection syringes.

5. Hermetic container for holding clinical waste, in accordance with claim 1, wherein the main portion (1) having a mouth embodies, in the area of the mouth (4) an outer skirt (3), arched outward and downward, while the cover (2) has a deep groove (5), capable of tightly accommodating the mouth (4) of the main portion, an outer wall of the cover extending in an ample skirt (6), arched in a manner similar to the outer skirt (3) of the main portion (1), oversized with respect to the outer skirt and provided with an inner perimetric flange designed to extend beyond a free edge of the outer skirt (3) of the main portion in order to hold the cover on the main portion and provide a leak-tight sealing.

* * * * *